US012802213B2

(12) United States Patent
Gong et al.

(10) Patent No.: US 12,802,213 B2
(45) Date of Patent: Nov. 17, 2026

(54) METHOD FOR ENHANCING QUALITY AND RESOLUTION OF CT IMAGES BASED ON DEEP LEARNING

(71) Applicant: Shanghai Radiodynamic Healthcare Technology, Shanghai (CN)

(72) Inventors: Nanjie Gong, Shanghai (CN); Jiachen Wang, Shanghai (CN)

(73) Assignee: Shanghai Radiodynamic Healthcare Technology, Shanghai (CN)

(*) Notice: Subject to any disclaimer, the term of this patent is extended or adjusted under 35 U.S.C. 154(b) by 501 days.

(21) Appl. No.: 18/255,608

(22) PCT Filed: Mar. 26, 2021

(86) PCT No.: PCT/CN2021/083307
§ 371 (c)(1),
(2) Date: Jun. 2, 2023

(87) PCT Pub. No.: WO2022/121160
PCT Pub. Date: Jun. 16, 2022

(65) Prior Publication Data
US 2024/0037732 A1 Feb. 1, 2024

(30) Foreign Application Priority Data
Dec. 7, 2020 (CN) ......................... 202011456115.3

(51) Int. Cl.
*G06K 9/00* (2022.01)
*G06T 3/4053* (2024.01)
(Continued)

(52) U.S. Cl.
CPC .......... *G06T 7/0012* (2013.01); *G06T 3/4053* (2013.01); *G06T 3/60* (2013.01); (Continued)

(58) Field of Classification Search
None
See application file for complete search history.

(56) References Cited

U.S. PATENT DOCUMENTS

2020/0273167 A1* 8/2020 Wilson .................. G06V 10/82
2022/0114699 A1* 4/2022 Hsiao ..................... G06N 3/045

OTHER PUBLICATIONS

Yang ("CT Image Denoising with Perceptive Deep Neural Networks", Arxiv.Org Cornell University Library 201 Olin Library Cornell University Ithaca NY, (Feb. 22, 2017), 8 pgs).*

* cited by examiner

*Primary Examiner* — Wei Wen Yang
(74) *Attorney, Agent, or Firm* — Dority & Manning, PA

(57) ABSTRACT

Disclosed in the present invention is a method for enhancing quality and resolution of CT images based on deep learning, comprising steps of: pre-processing collected clinical data to obtain a data set; building a deep learning model comprising a generative network, a discriminator network, and a perceptive network; building a loss function; using the data set and the loss function to update the parameters of the iterative generative network so as to obtain a trained deep learning model; and inputting a low-quality low-resolution image into the trained deep learning model to obtain a high-quality high-resolution image. The present invention may reduce the impact of spatial misalignment of data collected at different times due to movement of the patient or other reasons; and may implement end-to-end processing of the two tasks of enhancing CT image quality and super-resolution to directly obtain final results.

9 Claims, 3 Drawing Sheets

(51) Int. Cl.
*G06T 3/60* (2006.01)
*G06T 7/00* (2017.01)
*G16H 30/40* (2018.01)

(52) U.S. Cl.
CPC ... *G16H 30/40* (2018.01); *G06T 2207/10081* (2013.01); *G06T 2207/20132* (2013.01)

METHOD FOR ENHANCING QUALITY AND RESOLUTION OF CT IMAGES BASED ON DEEP LEARNING

FIELD

The invention relates to the technical field of image processing, in particular to a method for enhancing quality and resolution of CT images based on deep learning.

BACKGROUND

Computed tomography (CT) is one of the most important imaging and diagnostic methods for modern hospitals and clinics. In order to obtain high-quality and high-resolution CT images directly during scanning, it is necessary to increase the cost of scanning equipment and increase the radiation dose during scanning. However, according to related research, X-rays during CT scanning may cause genetic damage and induce cancer in a probability related to radiation dose. Therefore, in order to improve quality and resolution of CT images and avoid or reduce the risk of patients' health damage during scanning, it is necessary to reconstruct clinical CT data which contains a lot of noise and low resolution to obtain high-quality images with low noise and high resolution.

The methods of CT denoising image enhancement are generally divided into three categories: (A) sinogram filtering before reconstruction, (B) iterative reconstruction after reconstruction and (C) image post-processing after reconstruction. However, the sinogram data in method (A) is rarely provided directly to users, and this method may be affected by resolution loss and edge blur. Although method (B) greatly improve the image quality, they require high calculation cost, and the results may still lose some details and be affected by residual artifacts. Before the image post-processing based on deep learning, many post-processing methods have been proposed, such as NLM and K-SVD methods for CT denoising, and BM3D algorithm. However, due to the feature of uneven distribution of CT noise, they all have the defect of overly smoothness. Recently, the exploration of deep convolution network in CT denoising has achieved fruitful results. However, due to only the pixel-level MSE loss is used in performing the end-to-end training, the result will inevitably ignore the subtle image texture that is crucial to human perception, resulting in overly smooth edges and loss of details.

CT super-resolution methods are generally divided into two categories: (A) methods based on model reconstruction, and (B) methods based on learning. Among them, the first method explicitly models and regularizes the image degradation process, and reconstructs the data according to the characteristics of projection. Its effect depends on the accuracy of the assumed model. The methods based on learning will also face the problems of losing image details and producing block defects.

In the above-mentioned tasks of CT enhancement and super-resolution, the deep learning method often uses simulation data sets for training and evaluation, which often fails to reflect the performance when applying to real clinical data. Especially for the task of super-resolution, the super-resolution multiplier of clinical data is not fixed, which is different from the fixed multiplier in deep learning data sets. It can be seen that the current super-resolution task and the image enhancement task of CT images denoising cannot obtain high-quality, real-detailed images.

SUMMARY

The invention aims to solve the problem that image details are lost after denoising the images and implementing super-resolution processing in the prior art, and provides a method for enhancing quality and resolution of CT images based on deep learning.

The invention provides a method for enhancing quality and resolution of CT images based on deep learning, comprising steps of: S1, pre-processing collected clinical data to obtain a data set; S2, building a deep learning model comprising a generative network, a discriminator network, and a perceptive network; S3, building a loss function; S4, using the data set and the loss function to update parameters of the iterative generative network so as to obtain a trained deep learning model; and S5, inputting a low-quality low-resolution image into the trained deep learning model to obtain a high-quality high-resolution image.

Preferably, pre-processing clinical data in step S1 comprises steps of: S11, acquiring a low-quality CT image with low radiation dose and low resolution and a high-quality CT image with normal radiation dose and high resolution; S12, clipping the low-quality CT image according to metadata of a medical image, so that the clipped low-quality CT image corresponds to physical space information of the high-quality CT image, and a data pair with same physical space information is obtained; S13, clipping the data pair into patches of data pair, performing threshold determination, and reserving patches of data pair meeting a condition of the threshold determination; S14, performing pixel interception and normalization on the reserved patches of data pair; and S15, expanding data of the patches of data pair processed in step S14 so as to obtain the data set for training the deep learning model.

Preferably, clipping the data block into patches of data pair in step S13 comprises: clipping the high-quality CT image in the data block every fixed number of pixels/layers, and scaling a number of pixels/layers of the low-quality CT image corresponding to the high-quality CT image so as to correspond to the physical space information of the high-quality CT image.

Preferably, the condition of the threshold determination in step S13 is that a similarity index between the scaled low-quality CT image and the high-quality CT image in the patches of data pair is higher than a threshold.

Preferably, expanding data in step S15 includes flipping and rotating images.

Preferably, the loss function is a combined loss function of a mean absolute error loss, a perceptual loss and a generation countermeasure loss.

Preferably, the perceptual loss is obtained by inputting output result of the generative network and a real high-quality CT image into the perceptive network, respectively, and performing MSE loss on output result of the perceptive network.

Preferably, the generation countermeasure loss includes but is not limited to one of a GAN loss, a WGAN loss, a WGAN-GP loss or an rGAN loss.

Preferably, the generative network comprises a feature extraction module and an upsampling module, the feature extraction module comprises a convolution layer, cascaded convolution blocks, then passing through a convolution layer, and finally obtaining a low-resolution feature map from the low-quality CT image; each convolution block in the cascade convolution blocks comprises at least two 3*3*64 or other scale convolution layers and a middle ReLU layer; and the upsampling module comprises a fully connected network and a convolution layer, and each pixel position information of the input high-quality CT image is input into the fully connected network, and output result of the fully connected network is applied to the low-resolution feature map to obtain the high-quality high-resolution image.

Preferably, for the optimizer, Adam optimizer can be adopted to optimize the generative network and the discriminator network, but not limited to this.

The advantages of the present invention include: the present invention builds a deep learning model based on deep learning and pre-processes clinical data to obtain a data set, reducing the impact of spatial misalignment of data collected at different times due to movement of the patient or other reasons; by means of the deep learning model combined with the loss function, end-to-end processing of the two tasks of enhancing CT image quality and super-resolution can be implemented to directly obtain final results. The advantages further include that using the upsampling module in the generative network to achieve arbitrary scale of upsampling tasks.

DETAILED DESCRIPTION OF EMBODIMENTS

Figure 1:
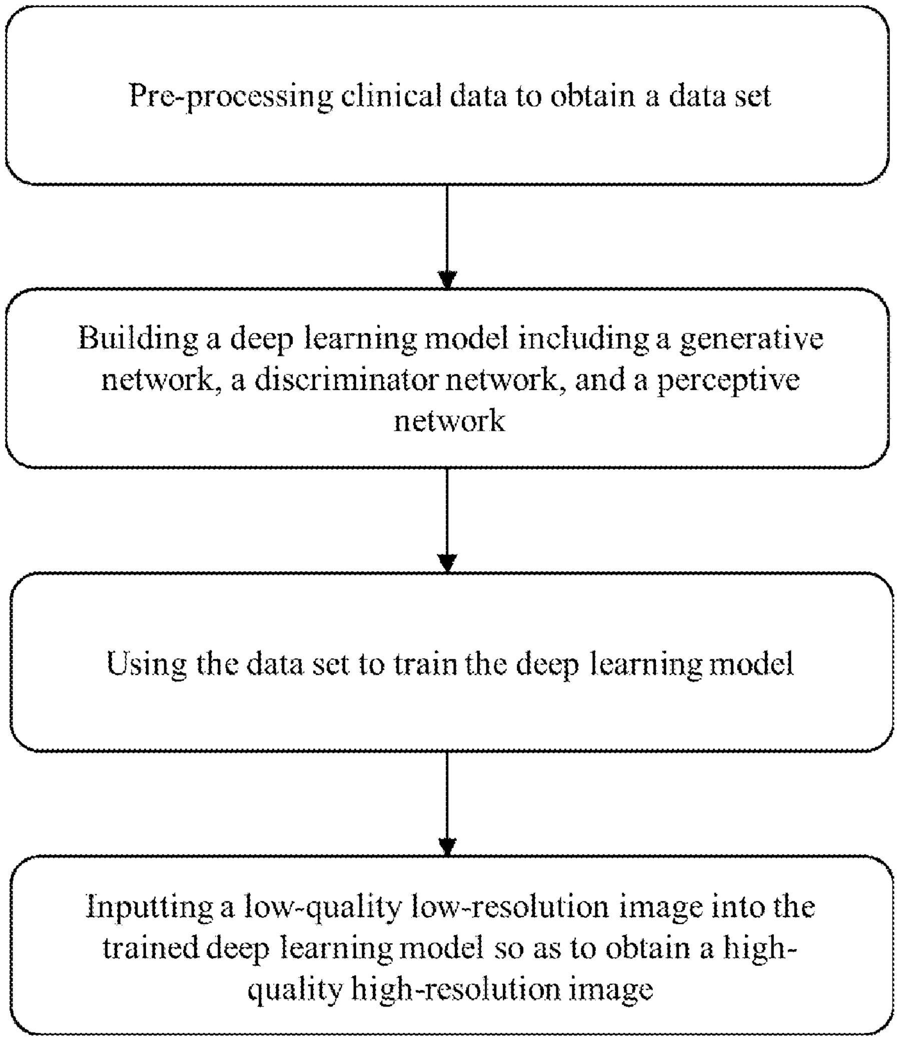
FIG. 1 is a flowchart of the main steps of a method for enhancing quality and resolution of CT images based on deep learning of the present invention.
Figure 2:
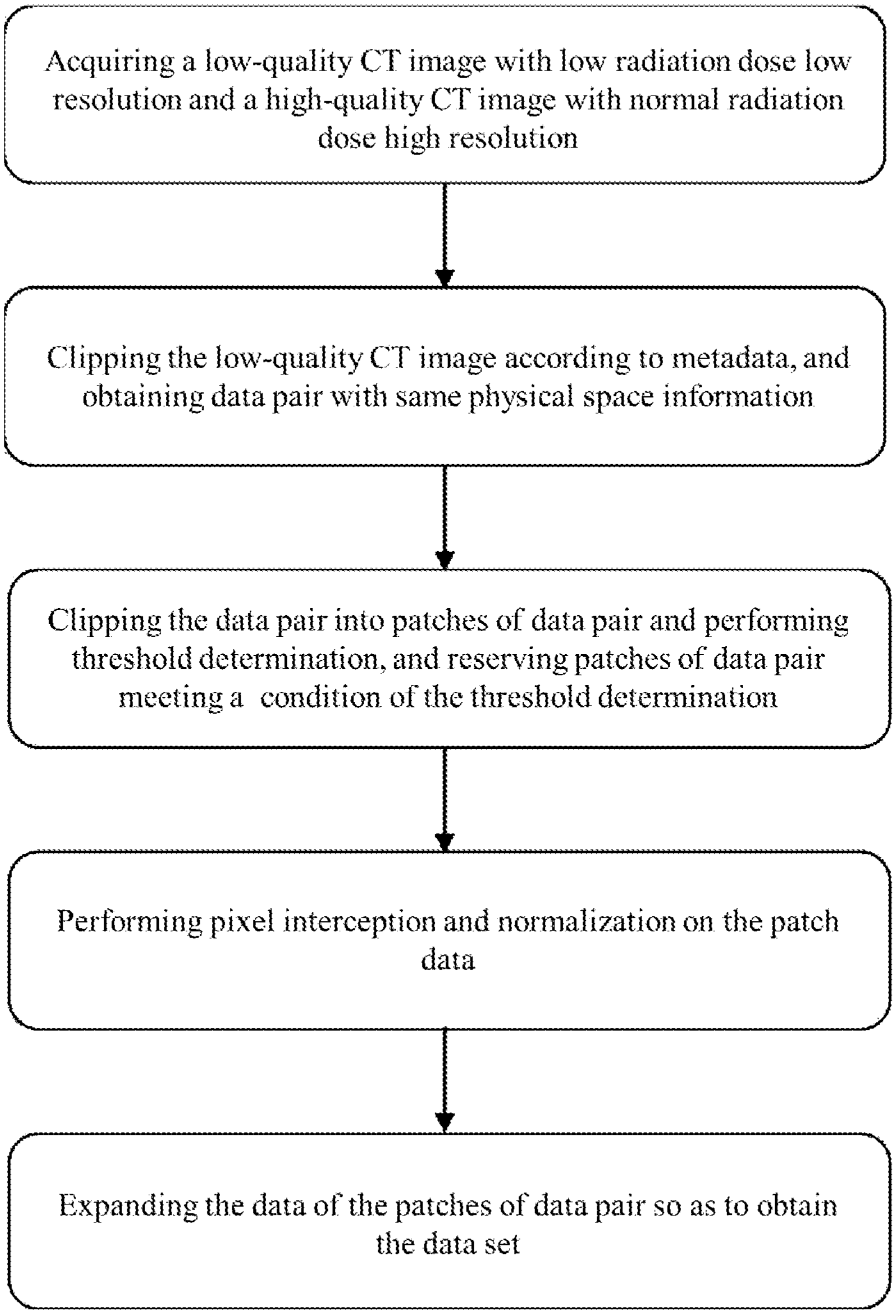
FIG. 2 is a flowchart of pre-processing clinical data in the embodiments of the present invention.
Figure 3:
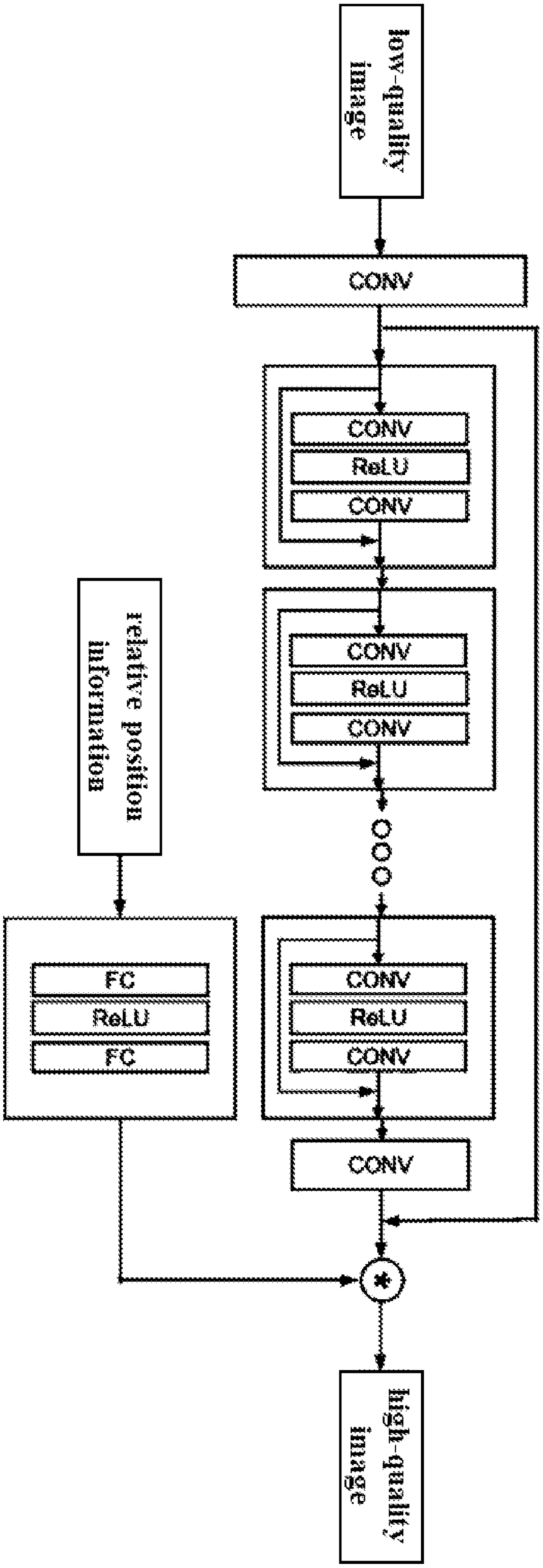
FIG. 3 is a structural diagram of a generative network in a deep learning model in the embodiments of the present invention.

The present invention will be further described in detail below with reference to specific embodiments and drawings. It should be emphasized that the following description is only exemplary, and is not intended to limit the scope and application of the present invention.

Non-limiting and non-exclusive embodiments will be described with reference to the following drawings, in which like reference numerals indicate like parts, unless otherwise indicated.

Embodiment 1

As shown in FIG. 1, the present embodiment provides a method for enhancing quality and resolution of CT images based on deep learning, which mainly includes the following steps:

S1: Pre-processing collected clinical data to obtain a data set.

S2: Building a deep learning model including a generative network, a discriminator network, and a perceptive network.

S3: Building a loss function.

S4: Using the data set and the loss function to update parameters of the iterative generative network so as to obtain a trained deep learning model.

S5: Inputting a low-quality low-resolution image into the trained deep learning model to obtain a high-quality high-resolution image.

Specifically, pre-processing clinical data in step S1 includes the following contents:

S11: Acquiring a low-quality CT image with low radiation dose and low resolution and a high-quality CT image with normal radiation dose and high resolution.

Successively acquiring, in a short time, global CT images with low radiation dose and low resolution (referred to as low-quality CT images) and CT images with normal radiation dose and high-resolution (referred to as high-quality CT images). That is, rapidly scanning twice by setting different scanning parameters. To reduce the time the patient is exposed to radiation, high-quality CT images do not need to be global images. Instead, they can be local images of the physical contents included in low-quality CT images. (For example, a low-quality whole lung CT image and a high-quality local lung CT image). In order to ensure that obvious resolution difference can be seen, the resolution multiplier may be required to be more than three times.

S12: Clipping the low-quality CT image according to metadata of a medical image, so that the clipped low-quality CT image corresponds to physical space information of the high-quality CT image, and a data pair with same physical space information is obtained.

According to metadata of a medical image (usually in DICOM type) containing spatial physical quantity information, clipping the low-quality CT image, such that it corresponds to the physical space information of (local) high-quality CT image, and a data pair with same physical space information is obtained. Among them, metadata includes indicators such as Pixel Spacing, SpacingBetweenSlices, ImagePositionPatients, and ImageOrientationPatients.

S13: Clipping the data pair into patches of data pair, performing threshold determination, and reserving patches of data pair meeting a condition of the threshold determination.

Synchronously traverse each of the data pair with same physical space information, and clip each data pair to obtain patches of data pair. (For high-resolution data, clip every fixed number of pixels/layers; for example, clip a patch of 96*96*3 for 48 pixels/2 layers. For low-resolution data, it needs to scale the corresponding pixel number or layer number to seek the correspondence with the physical space of high-resolution data). Perform threshold determination to the clipped patch of data pair. The condition of the determination is that: if the similarity index (including but not limited to PSNR and SSIM) between the scaled low-quality image patch and the high-quality image patch in the patch of data pair is higher than a certain value (threshold), then reserve the patch of data pair that meets the threshold, or otherwise it will be discarded. The threshold is specifically determined according to the super-resolution multiplier and the radiation difference.

S14: Performing pixel interception and normalization on the reserved patches of data pair.

Perform pixel value interception and normalization on the reserved patches of data pair. The pixel value interception is to avoid the patch pixel distribution is too sparse. The normalization is to facilitate the training of the later-level neural network. (For example, if the pixel value represents the CT value and the image is a lung CT image, the threshold can be set to be 1500; normalization is to linearly map the pixel value of [−1024,1500] to [−1,1]).

S15. Expanding the data of the patches of data pair processed in step S14 in order to obtain a data set for training the deep learning model. Data may be expanded in the manner of image flipping and rotating.

The concept of the present invention is that: when training the deep learning model, the input of the deep learning model is the batch data consisting of low-quality image patch data, and the desired output to be obtained shall be the same as the batch data consisting of high-quality image patch data as much as possible. After the training, the obtained deep learning model can output the input low-quality and low-resolution CT image as the high-quality and high-resolution CT image.

In the present embodiment, the deep learning model includes a generative network, a discriminator network, and a perceptive network. The generative network includes the following contents:

(a) Feature extraction module: A preliminary feature extraction is performed by a convolution layer (in the present embodiment, 64 convolution kernels with a size of 3*3 and a step size of 1 are used to obtain 64 layers of features); then the main computing unit is formed by the cascaded basic convolution blocks and the last layer of the convolution layers (in the present embodiment, it is set as a cascade of 16 basic convolution blocks, and each basic block includes two 3*3*64 convolution layers and a ReLU layer in the middle); finally, a low-resolution feature map is obtained by the low-quality CT image. The result of the main computing unit and the result of the preliminary feature extraction are added to form a residual structure. The above is the feature extraction module of the generative network.

(b) Upsampling module: In order to achieve arbitrary scale of super-resolution, the upsampling module can learn the number of convolution kernels and the weight parameters corresponding to upsampling with different factors. The upsampling module consists of a fully connected network (which may consists of a 256-node fully connected layer+ReLU+a 256-node fully connected layer) and a corresponding convolution layer. Among them, the input of the fully connected network is the pixel position information of the high-resolution image (the pixel position information of the high-resolution image refers to the relative offset between the actual value of the corresponding pixel coordinate of the low-resolution image corresponding to each pixel coordinate and the rounding value of the corresponding pixel coordinate of the low-resolution image corresponding to each pixel coordinate in the high-resolution image) and the scale factor, and output the same number of filter kernels as the number of pixels of the high-resolution image. The implementation flow of the upsampling module is as follows: for each pixel in the high-resolution image, its position information is input into the above-mentioned fully connected network to obtain a filter kernel; then each of the output filter kernel is applied to the corresponding position of the low-resolution feature map (the result of the computing unit) (the corresponding position refers to the pixel position of the high-resolution image mapped to the corresponding position of the low-resolution feature map); the corresponding pixel value in the high-resolution image may be obtained, and the high-resolution image may be obtained by traversing all pixel positions in the high-resolution image.

The discriminator network is used to form a GAN structure with the generative network part to improve the training quality, such that the result details output by the generative network are richer and more real. Part of the discriminator network can use a variety of binary network structures. The following structure can be set in the experiment: a convolution kernel, a batch normalization layer and a ReLU layer consist of the basic unit, and seven basic units are cascaded to form the feature extraction part. Among them, every other basic unit, the convolution step size in the following basic unit is adjusted to 2, and the number of convolution kernels is doubled. The feature extraction part is follow by a classification module. The classification module obtains a numerical result from a 1024-node fully connected layer+ReLU+fully connected layer, which characterizes the probability that the input image is a high-quality and high-resolution image. The perceptive network part may adopt VGG16 network or VGG19 network.

Specifically, in the training of the deep learning model in step S4, the loss function used in the training is a combined loss function of a mean absolute error loss, a perceptual loss and a generation countermeasure loss. Among them, the perceptual loss is obtained by inputting output result of the generative network and a real high-quality CT image into the perceptive network, respectively, and performing MSE loss on output result of the perceptive network. The generation countermeasure loss includes but is not limited to one of a GAN loss, a WGAN loss, a WGAN-GP loss or an rGAN loss. For the optimizer, Adam optimizer can be adopted to optimize the generative network and the discriminator network, but not limited to this.

A more detailed training process of the deep learning model is as follows:

(1) Sending low-quality image patch data in the same batch of data set to the generative network part, in which one batch is set as 16 patches of data pair.

(2) Comparing the super-resolution result obtained in (1) with the high-quality image patch data in the same batch of data set, and calculating the mean absolute error loss.

(3) Sending the super-resolution result obtained in (1) and the high-quality image patch data in the same batch of data set to the perceptive network to obtain the corresponding output feature map of the perceptive network, and obtaining the perceptual loss by calculating the mean absolute error loss for the feature map.

(4) Sending the super-resolution result obtained in (1) and the high-quality image patch data in the same batch of data set to the discriminator network to obtain the corresponding output value of the discriminator network (the output value represents the meaning that: the probability that the discriminator network determines the input as a high-quality image), and obtaining the generation countermeasure loss by calculating the generator loss in the corresponding GAN loss (the GAN loss can be a basic GAN loss, or a WGAN-GP loss or an rGAN loss, etc.).

(5) Fixing the parameters of the discriminator network and the perceptive network. According to the mean absolute error loss, the perceptual loss, and the generation loss part in the GAN loss (i.e., generation countermeasure loss), updating the parameters in the generative network by Adam optimizer.

(6) Sending the super-resolution result obtained in (1) and the high-quality image patch data in the same batch of data set into the discriminator network to obtain the corresponding output value of the discriminator network, and obtaining the decider loss in the corresponding GAN loss (the GAN loss can be a basic GAN loss, or a WGAN-GP loss or an rGAN loss, etc.) by calculating.

(7) Repeating (1)-(6) until the mean absolute error loss and the perceptual loss converge. The training completed.

Embodiment 2

Different from Embodiment 1, in the present embodiment, the pre-processing method of pre-processing the collected clinical data to obtain a data set is: obtaining a low-quality CT image with the same size as a high-quality CT image by using three-dimensional interpolation, and clipping to obtain patches of data pair.

The generative network may, but not limited to, adopt U-Net structure. The decider may be, but not limited to, Patch GAN. The use of Patch GAN may take in account the influence of different parts of the image, solving the problem of inaccurate output images caused by only one corresponding output for one input.

Different from the simulation training set used in the prior art, the present invention obtains the real training data set by pre-processing the real clinical data, so that the deep learning model can be applied to clinical practice. By using the framework of generation countermeasure network, in conjunction with the perceptual loss and the pixel-level loss, the deep learning model of the present invention may end-to-end realize the optimization of low-radiation and low-resolution medical images which have no clinical use value into high-quality and high-resolution medical images. Meanwhile, the tasks of denoising low-radiation CT images and super-resolution of low-resolution CT images can be realized simultaneously, such that the generated high-quality images have real details. The deep learning model provided in the present invention may also be used for other image enhancement tasks by changing the data set, such as denoising or super-resolution of natural images. In a preferred embodiment, an arbitrary scale factor for super-resolution may be realized by introducing an upsampling module of any scale factor.

Those skilled in the art will realize that various modifications to the above description are possible. So, the embodiments and drawings are only used to describe one or more specific implementations.

Although exemplary embodiments that are regarded as the present invention have been described and illustrated, those skilled in the art will understand that various changes and replacements can be made thereto without departing from the spirit of the present invention. In addition, many modifications may be made to adapt a particular situation to the teachings of the present invention without departing from the central concept of the present invention described herein. Therefore, the present invention is not limited to the specific embodiments disclosed herein, and the present invention may also include all embodiments and their equivalents within the scope of the present invention.

What is claimed is:

1. A method for enhancing quality or resolution of CT images based on deep learning, characterized by comprising steps of:

S1, pre-processing collected clinical data to obtain a data set;

S2, building a deep learning model comprising a generative network, a discriminator network, and a perceptive network;

S3, building a loss function;

S4, using the data set and the loss function to update parameters of the iterative generative network so as to obtain a trained deep learning model; and S5, inputting a low-quality low-resolution image into the trained deep learning model to obtain a high-quality high-resolution image, wherein the generative network comprises a feature extraction module and an upsampling module, the feature extraction module comprises a convolution layer, cascaded convolution blocks, then passing through a convolution layer, and finally obtaining a low-resolution feature map from the low-quality CT image; each convolution block in the cascade convolution blocks comprises at least two convolution layers and a middle ReLU layer; and the upsampling module comprises a fully connected network and a convolution layer and achieves arbitrary scale of super-resolution, and each pixel position information of a high-quality CT image and a scale factor are inputted into the fully connected network to output the same number of filter kernels as the number of pixels of the high-quality CT image, and each of the output filter kernels of the fully connected network is applied to the low-resolution feature map to obtain the high-quality high-resolution image.

2. The method for enhancing quality or resolution of CT images based on deep learning according to claim 1, characterized in that, pre-processing clinical data in step S1 comprises steps of:

S11, acquiring a low-quality CT image with low radiation dose low resolution and the high-quality CT image with normal radiation dose high resolution;

S12, clipping the low-quality CT image according to metadata of a medical image, so that the clipped low-quality CT image corresponds to physical space information of the high-quality CT image, and a data pair with same physical space information is obtained;

S13, clipping the data pair into patches of data pair, performing threshold determination, and reserving patches of data pair meeting a condition of the threshold determination;

S14, performing pixel interception and normalization on the reserved patches of data pair; and S15, expanding data of the patches of data pair processed in step S14 so as to obtain the data set for training the deep learning model.

3. The method for enhancing quality or resolution of CT images based on deep learning according to claim 2, characterized in that, clipping the data pair into patches of data pair in step S13 comprises:

clipping the high-quality CT image in the data pair every fixed number of pixels/layers, and scaling a number of pixels/layers of the low-quality CT image corresponding to the high-quality CT image so as to correspond to the physical space information of the high-quality CT image.

4. The method for enhancing quality or resolution of CT images based on deep learning according to claim 3, characterized in that, the condition of the threshold determination in step S13 is that a similarity index between the scaled low-quality CT image patch and the high-quality CT image patch in the patches of data pair is higher than a threshold.

5. The method for enhancing quality or resolution of CT images based on deep learning according to claim 2, characterized in that, expanding data in step S15 includes flipping and rotating images.

6. The method for enhancing quality or resolution of CT images based on deep learning according to claim 1, characterized in that, the loss function is a combined loss function of a mean absolute error loss, a perceptual loss and a generation countermeasure loss.

7. The method for enhancing quality or resolution of CT images based on deep learning according to claim 6, characterized in that, the perceptual loss is obtained by inputting output result of the generative network and a real high-quality CT image into the perceptive network, respectively, and performing MSE loss on output result of the perceptive network.

8. The method for enhancing quality or resolution of CT images based on deep learning according to claim 6, characterized in that, the generation countermeasure loss is one of a GAN loss, a WGAN loss, a WGAN-GP loss or a rGAN loss.

9. The method for enhancing quality or resolution of CT images based on deep learning according to claim 1, characterized in that, optimizer is adopted to optimize the generative network and the discriminator network.

* * * * *